United States Patent [19]

Kakino

[11] 4,332,161

[45] Jun. 1, 1982

[54] ACOUSTIC DETECTION OF TOOL WEAR AND FRACTURE

[75] Inventor: Yoshiaki Kakino, Kyoto, Japan

[73] Assignee: NL Circuit Design Block Co., Ltd., Japan

[21] Appl. No.: 116,509

[22] Filed: Jan. 29, 1980

[30] Foreign Application Priority Data

Jan. 31, 1979 [JP] Japan .............................. 54-010107

[51] Int. Cl.³ ........................................... G01N 19/00
[52] U.S. Cl. ................................................... 73/104
[58] Field of Search ........................ 73/587, 593, 104

[56] References Cited

U.S. PATENT DOCUMENTS

| | | | |
|---|---|---|---|
| 3,400,578 | 9/1968 | Frarey et al. ........................... | 73/593 |
| 3,548,648 | 12/1970 | Weichrrodt et al. ................. | 73/104 |
| 3,713,127 | 1/1973 | Keledy et al. ......................... | 73/587 |
| 3,793,627 | 2/1974 | Darrel et al. .......................... | 73/104 |
| 3,841,149 | 10/1974 | Edwin et al. .......................... | 73/104 |
| 4,087,801 | 5/1978 | Noh ........................................ | 73/104 |

Primary Examiner—Anthony V. Ciarlante
Attorney, Agent, or Firm—William A. Drucker

[57] ABSTRACT

For detecting brittle fracture and wear of a tip of a cutting tool an acoustic emission monitoring system has a converter for converting acoustic emission into an electric signal, a filter for rejecting frequency components in the signal below a frequency between 50 kHz and 300 kHz, a detector to detect the amplitude of the signal after the rejection of those frequency components, and a comparator for comparing that amplitude to a predetermined reference amplitude.

4 Claims, 3 Drawing Figures

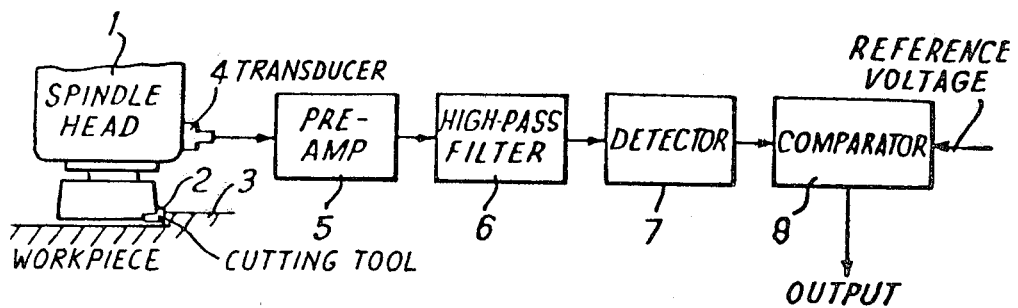
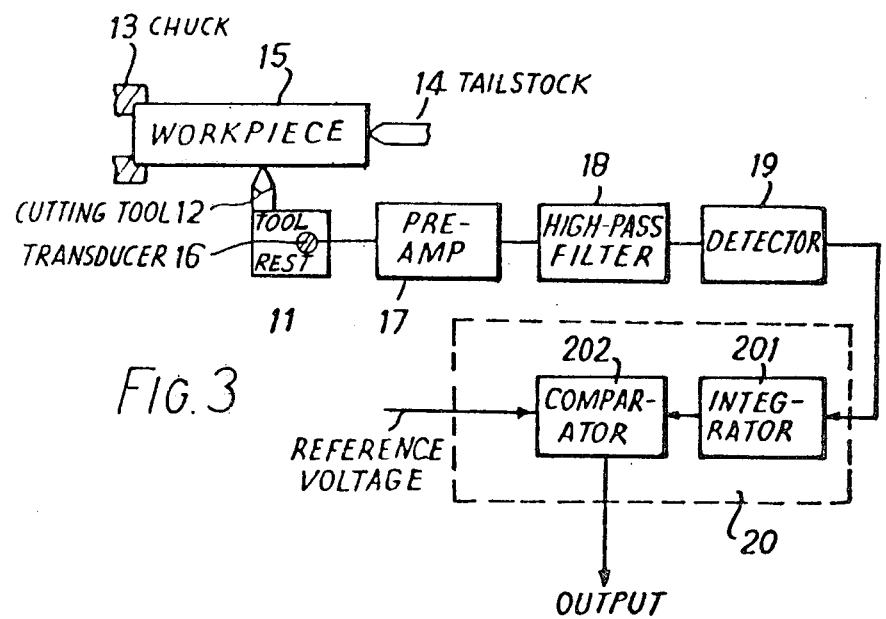

ACOUSTIC DETECTION OF TOOL WEAR AND FRACTURE

BACKGROUND OF THE INVENTION

The present invention relates to a method and apparatus with which brittle fracture or wear and tear of cutting tools can be detected by taking advantage of acoustic emission technology.

To continue a cutting operation with a fractured tool tip can cause not only damage to a machine tool but also hazard to the operator.

THE PRIOR ART

A method of detecting fracture is known wherein the total acoustic emission generated during machining is monitored and its amplitude compared with a predetermined reference level. The main sources of acoustic emission during machining are (a) shear zones in the material being plastically deformed, (b) the bending of parts of chips at a chip breaker, (c) contacting of a point of a chip with the material or with the machine, and (d) a fractured or worn part of the tip.

In most cases, unfortunately, the acoustic emission from the above-mentioned sources (a), (b) and (c), due to the deformation of the material being cut is far larger than that from the source (d) which it is most interesting to detect.

By the conventional method which monitors total acoustic emission, the failure of the tool can therefore only be detected when conditions of cutting are kept constant, so that the fluctuations of the acoustic emission amplitude due to the deformation is very low.

But in more general cases, such as intermittent cutting or cutting with varying chip removal rate caused by non-uniform speed and/or depth of cutting, the fluctuations of the acoustic emissions from the sources (a),(b) and (c) mentioned above are large enough to make it impossible to discriminate the increase of acoustic emission due to the failure of the tool.

OBJECT OF THE INVENTION

The object of the present invention is to provide a method and apparatus wherein brittle fracture and/or wear of a cutting tool can be detected with high reliability by detecting the acoustic emission caused only by the fracture and/or wear, while ignoring acoustic emission from other causes.

BRIEF DESCRIPTION OF THE DRAWINGS

The invention will be best understood by reference to the accompanying drawings.

In the drawings:

FIG. 2 is a block diagram of a fracture detector in accordance with the invention;

FIG. 3 is a block diagram of another embodiment of wear detector in accordance with the invention.

DESCRIPTION OF THE PREFERRED EMBODIMENT

Figure 1:
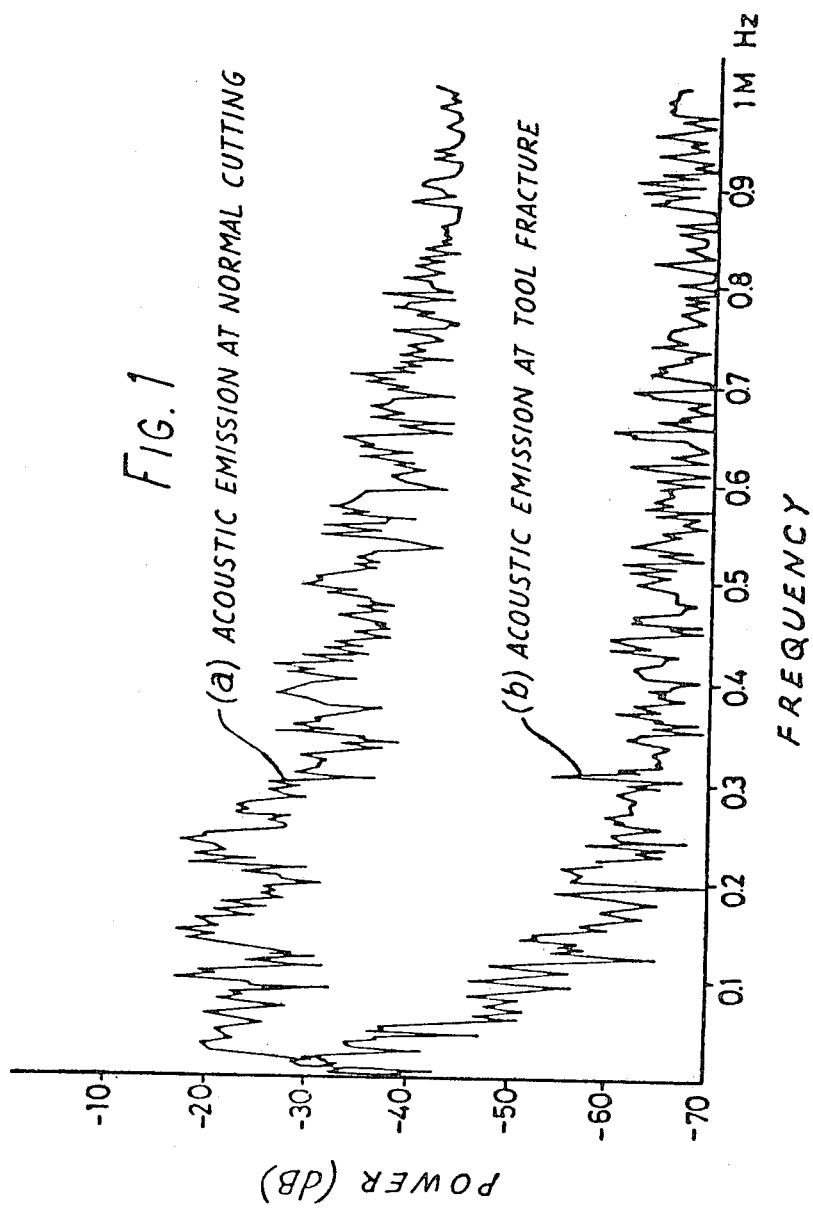
FIG. 1 is a graphical representation of a typical power spectrum of an acoustic emission generated during machining.

FIG. 1 shows a result of an experiment for the study of the power spectrum of an acoustic emission. In this work, carbon steel S48C (0.48 plain carbon content) and a sintered carbide tip P20 were used respectively as the material to be cut and as the tool, and the cutting conditions were as follows: cutting speed: 120 m/min, depth of cut: 2 mm, feed: 0.4 mm/rev.

In FIG. 1, curves (a) and (b) show the power spectrum of the acoustic emission generated from the shear zone of the material being cut, and that due to the fracture of the cutting tool, respectively. It is obvious from this result that most of the energies of the acoustic emission due to the two causes mentioned above lie in different frequency bands.

It can be seen that the relative amplitudes along the power axis, for curve (a) general noise, and curve (b) (tool fracture noise) is of about the same order for frequencies up to about 50 KHz, and that above 300 KHz the output of a high pass filter would tend to be low and give a poor signal-to-noise ratio. It is only in the zone from 50 KHz to 300 KHz that discrimination becomes possible.

Accordingly, the acoustic emission caused by a fracture of the tip can be detected by measuring the amplitude through a high-pass filter with an appropriate cutoff frequency. When this cutoff frequency is set at a frequency lower than 50 kHz the acoustic emission due to the deformation of the work material and that due to the fracture may have comparable amplitude at the output of the high-pass filter, so that discrimination of the latter from the former is critical.

On the other hand, when the cutoff frequency is set at higher than 300 kHz, the output level of the high-pass filter becomes low, resulting in a poor signal-to-noise ratio, because a large amount of the energy of the emission from the fracture of the tip will be attenuated by the stop-band characteristic of the filter.

According to many experiments performed, it is in practice essential to choose the cutoff frequency within the range from 50 kHZ to 300 kHz in order to achieve a reliable detection of fractures of the tools.

The present invention may best be described with reference to FIG. 2. The embodiment described therein comprises an acoustic emission transducer 4, a preamplifier 5, a high-pass filter 6, a detector 7 and a comparator 8. In this figure, reference numeral 1 indicates a spindle head of a milling machine, and 2 indicates a cutting tool which is cutting material 3.

The transducer 4 is attached to the spindle head. The output voltage of the transducer is amplified by the preamplifier and then applied to the detector after passing through the high-pass filter 6. Since the cutoff frequency of the high-pass filter is set to 100 kHz, the dominant component of the acoustic emission from the deformation of the work material is almost eliminated and the acoustic emission signal due to the facture of the tip alone can be taken out at the output of the filter. This acoustic emission signal is sent to the amplitude detector 7 and the output of the detector is applied to the comparator to be compared with a reference voltage representing an allowable size and state of the fracture. When the input signal exceeds the reference voltage, a signal is obtained at the output of the comparator 8. This signal may be utilized for immediate stoppage of the machining to avoid the consequential loss, by linking it to the controller of the machine.

The acoustic emission signal due solely to the fracture of the tool alone can be detected by the above-described system, even when it is accompanied by a widely fluctuating level of acoustic emission due to the deformation of the material being cut.

An alternative embodiment is shown in FIG. 3 wherein the invention provides an apparatus to detect wear of a tool used in a lathe. In FIG. 3 reference numerals 11 and 12 respectively denote a tool rest and a cutting tool, and a cutting operation is performed between the cutting tool 12 and the work material 15 which is supported by a chuck 13 and a tail stock 14. A transducer 16 is installed on the tool rest 11 and a preamplifier 17, a high-pass filter 18 and a detector 19 are connected to the transducer in cascade in the same way as in FIG. 2.

The output of the detector is sent to a discriminator circuit 20 which comprises an integrator 201 and a comparator 202. The integrator integrates the output of the detector at fixed intervals of time and the output of this integrator is compared with a predetermined reference voltage by the comparator which generates an alarm signal when the output of the integrator exceeds the reference voltage.

In this embodiment, the acoustic emission signal generated by machining of the work material 15 with the cutting tool 12 is detected by the transducer 16, amplified by the amplifier 17, and sent to the discriminator circuit 20 through the filter 18 and the detector 19 by which the acoustic emission due to the wear of the cutting tool alone is selected and detected.

In this discriminator circuit an integrator 201 connected to the detector is controlled so as to integrate the output voltage of the detector for a certain finite period. At the end of this period the integrator is re-set to zero. These cycles of operations are repeated, and the output of the integrator is compared with a reference voltage in a comparator 202.

In this configuration, the acoustic emissions caused by wear of the cutting tip alone are rectified, and its amplitude is integrated with respect to time. The output voltage of the integrator just before the end of the period relates closely to the degree of wear of the tool, and increases as the wear progresses., Therefore, if the reference voltage is set at the value corresponding to the maximum allowable degree of wear, the end of the life of the tool can be indicated by the output state of the comparator.

Various changes and modifications may be made within the scope of the invention as set forth in the appended claims. For example, the reference voltage may preferably be floating instead of being constant, in case the acoustic emission from the deformation zone is so large and fluctuating that the output of the high-pass filter contains a considerable amount of acoustic emission signal with varying amplitude even with normal machining. The floating reference voltage may be obtained by rectifying the output of the filter, adding a constant dc voltage, and making it pass through a simple delay circuit.

Many modifications may be made with regard to the means to eliminate the acoustic emission generated from the deformation zone of the work material. The high-pass filter may be replaced by a band-pass filter or a transducer with a frequency characteristic suitable to eliminate the unnecessary acoustic emissions. The present invention may be applied not only to milling machines and lathes, but also to various other kinds of machine tools using cutting tools.

We claim:

1. An acoustic emission monitoring system, for detecting brittle fracture and wear of a tip of a cutting tool, comprising means for converting acoustic emission into an electric signal, a high-pass filter for rejecting frequency components in said signal lower than a frequency selected in the range 50 KHz to 300 KHz inclusive, means for detecting the amplitude of said signal after rejecting said frequency components, and means for comparing said amplitude with a predetermined reference amplitude.

2. A method of detecting brittle fracture and wear of a tip of a cutting tool comprising the steps of converting acoustic emission into an electric signal, rejecting frequency components in said signal lower than a frequency selected in the range 50 KHz to 300 KHz inclusive, detecting the amplitude of said signal after rejection of said frequency components, and comparing said amplitude with a predetermined reference amplitude.

3. The method claimed in claim 2 comprising the further step of integrating said amplitude for a predetermined period to evaluate the wear of said tip of said tool.

4. An acoustic emission monitoring system, for detecting brittle fracture and wear of a tip of a cutting tool, comprising:
 (i) means for converting acoustic emission into an electric signal;
 (ii) a high-pass filter for rejecting frequency components in said signal lower than a frequency selected in the range 50 kHz to 300 kHz inclusive,
 (iii) means for detecting the amplitude of said signal after rejecting said frequency components,
 (iv) means for integrating the detected amplitude, and
 (v) means for comparing the integrated amplitude with a predetermined reference amplitude.

* * * * *